United States Patent [19]
Kandimalla et al.

[11] Patent Number: 5,886,165
[45] Date of Patent: *Mar. 23, 1999

[54] MIXED BACKBONE ANTISENSE OLIGONUCLEOTIDES CONTAINING 2'-5'-RIBONUCLEOTIDE- AND 3'-5'-DEOXYRIBONUCLEOTIDES SEGMENTS

[75] Inventors: Ekambar R. Kandimalla, Worcester; Sudhir Agrawal, Shrewsbury, both of Mass.

[73] Assignee: Hybridon, Inc., Milford, Mass.

[*] Notice: This patent issued on a continued prosecution application filed under 37 CFR 1.53(d), and is subject to the twenty year patent term provisions of 35 U.S.C. 154(a)(2).

[21] Appl. No.: 719,970

[22] Filed: Sep. 24, 1996

[51] Int. Cl.$^6$ .............................. C07H 21/02; C07H 21/04
[52] U.S. Cl. ......................... 536/23.1; 536/24.5; 514/44; 435/6
[58] Field of Search .............................. 514/44; 536/23.1, 536/24.5; 436/6

[56] References Cited

U.S. PATENT DOCUMENTS

| | | | |
|---|---|---|---|
| 5,149,797 | 9/1992 | Pederson et al. | 536/23.1 |
| 5,194,428 | 3/1993 | Agrawal et al. | 514/44 |
| 5,521,161 | 5/1996 | Malley et al. | 514/45 |
| 5,532,130 | 7/1996 | Alul | 435/6 |

FOREIGN PATENT DOCUMENTS

| | | |
|---|---|---|
| 0639607 | 2/1995 | European Pat. Off. . |
| 9112323 | 8/1991 | WIPO . |
| 9401550 | 1/1994 | WIPO . |
| 9417091 | 8/1994 | WIPO . |
| 9423028 | 10/1994 | WIPO . |
| 9532986 | 12/1995 | WIPO . |
| 9711171 | 3/1997 | WIPO . |

OTHER PUBLICATIONS

Agrawal et al.(II), "Mixed–Backbone Oligonucleotides as Second Generation Antisense Oligonucleotides" In Vitro and In Vivo Studies, *Proc. Nat. Acad. Sciences USA.* 94(6), 2620–2625 (Mar. 18, 1997).
Zon, "Oligonucleotide Analogues as Potential Chemotherapeutic Agents," *Pharmaceutical Research*, 5(9), 539–549 (1988).
Gura, "Antisense Has Growing Pains—Efforts to Develop Antisense Compounds for Cancer, AIDS, and Other Diseases Have Encountered Some Unexpected Questions About How the Drugs Really Work," *Science*, 270, 575–577 (Oct. 27, 1995).
Agrawal and Iyer, *Current Opin. Biotech.* 6, 12–19 (1995), Issue No. 4.
Agrawal et al., *Biochem. Pharmacol.* 50, 571–576 (1995).
Agrawal et al., *Proc. Natl. Acad. Sci. USA* 85, 7079–7083 (Oct. 1988).
Agrawal et al., *Proc. Natl. Acad. Sci. USA* 87, 1401–1405 (Feb. 1990).
Agrawal et al., *Toxicology Letts.* 82/83, 431–434 (1995).
Agrawal, *Clin. Pharmacokinet.* 28, 7–16 (1995), Issue No. 1.
Agrawal, *Trends in Biotechnology* 10, 152–158 (May 1992).
Barker et al., *Proc. Natl. Acad. Sci. USA* 93, 514–518 (Jan. 1996).
Bayever et al., *Antisense Res. Dev.* 3, 383–390 (1993).
Beaucage, *Methods in Molecular Biology, vol. 20, Oligonucleotides and Analogs*, pp. 33–62 (S. Agrawal, ed., Humana Press, Totowa, New Jersey), 1993).
Cedergren and Grosjean, *Biochem. Cell. Biol.* 65, 677–692 (1987).
Crooke et al., *Clin. Pharm. Therap.* 56, 641–646 (Dec. 1994).
"Dyad's patented oligonucleotides may lead to treatments for male pattern baldness," *Biotech Patent News* 10(8), 6 (Aug. 1996).
Dougherty et al., *J. Am. Chem. Soc.* 114, 6254–6255 (1992).
Galbraith et al., *Antisense Res. Dev.* 4, 201–206 (1994).
Giannaris and Damha, *Nucleic Acids Res.* 21, 4742–4749 (1993), Issue No. 20.
Hashimoto and Switzer, *J. Am. Chem. Soc.* 114, 6255–6256 (1992).
Holt et al., *Mol. Cell Biol.* 8, 963–973, Issue No. 2, Feb. 1988).
Jin et al., *Proc. Natl. Acad. Sci. USA* 90, 10568–10572 (Nov. 1993).
Kandimalla et al., *Nucleic Acids Res.* 23, 3578–3584 (1995), Issue No. 17.
Kerr and Brown, *Proc. Natl. Acad. Sci. USA* 75, 256–260 (Jan. 1978).
Kierzek et al., *Nucleic Acids Res.* 20, 1685–1690 (1992), Issue No. 7.
Kitajima et al., *Science* 258, 1792–1795 (Dec. 11, 1992).
Kondo et al., *Biochem.* 9, 3479–3498 (1970), Issue No. 18.
Krieg et al., *Nature* 374, 546–549 (Apr. 6, 1995).
Lalitha and Yathindra, *Current Sciences* 68, 68–75 Issue No. 1 (Jan. 1995).
Lesiak et al., *J. Biol. Chem.* 258, 13082–13088, Issue No. 21, Nov. 10, 1983.
Matsukura et al., *Proc. Natl. Acad. Sci. USA* 84, 7706–7710 (Nov. 1987).

(List continued on next page.)

*Primary Examiner*—Marian C. Knode
*Assistant Examiner*—L. Eric Crane
*Attorney, Agent, or Firm*—McDonnell Boehnen Hulbert & Berghoff

[57] ABSTRACT

The present invention provides a novel class of oligonucleotides useful for antisense purposes. The oligonucleotides of the invention comprise both deoxyribonucleotides with "natural" 3'–5' internucleotide linkages and ribonucleotides with 2'–5' internucleotide linkages. Because of their conformation structure, oligonucleotides according to the invention possess uniform intra-phosphate distances throughout the oligonucleotide chain, allowing them to bind efficiently to complementary DNA and RNA with "natural" 3'–5' internucleotide linkages. The oligonucleotides according to the invention advantageously exhibit diminished immune stimulation and significantly reduced effect on both complement and coagulation as compared to 3'–5' oligonucleotides.

15 Claims, 10 Drawing Sheets

OTHER PUBLICATIONS

Michelson and Monny, *Biochim. Biophys. Acta* 149, 107–126 (1967).
Nesterova and Cho–Chung, *Nature Medicine* 1, 528–533, Issue No. 1 (Jun. 1995).
Offensperger et al., *EMBO J.* 12, 1257–1262 (1993), Issue No. 3.
Padget et al., *Science* 225, 898–903 (Aug. 31, 1984).
Puglisi and Tinoco, *Methods in Enzymology*, vol. 180, pp. 304–325 (Dahlberg and Abelson, eds., Academic Press, San Diego, CA) 1989.
Ratajczak et al., *Proc. Natl. Acad. Sci. USA* 89, 11823–11827 (Dec. 1992).
Sands et al. *Mol. Pharmacol.* 45, 932–943 (1994).
Sarin et al., *Proc. Natl. Acad. Sci. USA* 85, 7448–7451 (Oct. 1988).
Sawai et al., *J. Biomol. Structure Dyn.* 13, 1045–1051 (1996), Issue No. 6.
Schatz et al., *EMBO J.* 9, 1171–1176 (1990), Issue No. 4.
Seki et al., Nucleic Acids Symp. Series 29, 71–72 (Nov. 9, 1993).
Simons et al., *Nature* 359, 67–70 (Sep. 3, 1992).
Smith et al., *Proc. Natl. Acad. Sci. USA* 83, 2787–1791 (May 1986).
Tazawa et al., *Biochem.* 8, 3499 (1970), Issue No. 18.
Thoung et al., *Angew. Chem Int. Ed. Engl.* 32, 666–690 (1993).
Ts'o et al., *Biochem.* 8, 997–1029 (1969), Issue No. 3.
Uhlmann and Peyman, *Chem Rev.* 90, 543–584, Issue No. 4. (Jun. 1990).
Usher and McHale, *Proc. Natl. Acad. Sci. USA* 73, 1149–1153 (1976), Issue No. 4 (Apr. 1976).
Westheimer, *Acc. Chem. Res.* 1, 70–78. (Mar. 1968).
Zamecnik and Stephenson, *Proc. Natl. Acad. Sci. USA* 75, 280–284, Issue No. 1 (Jan. 1978).
Zhang et al., *Biochem. Pharmacol.* 49, 929–939 (1995), Issue No. 7.
Zhang et al., *Biochem. Pharmacol.* 50, 545–556 (1995), Issue No. 4.
Zhang et al., *Clin. Pharm. Therap.* 58, 44–53, Issue No. 1 (Jul. 1995).
Zhao et al., *Biochem. Pharmacol.* 51, 173–182 (1996).

| SEQ ID NO | Modified Backbone and Control Oligonucleotides |
|---|---|
| 1 | 5'-C*U*C*d(TCGCACCCATCTCTCTCC)U*U*C*d(T)-3' |
| 2 | 5'-C*U*C*d(TCGCACCCATCTCTCTCC)U*U*C*d(T)-3' |
| 3 | 5'-C*U*C*d(TCGCACCCATCTCTCTCC)U*U*C*d(T)-3' |
| 4 | 5'-C*U*C*d(TCGCACCC)A*U*C*d(TCTCTCC)U*U*C*d(T)-3' |
| 5 | 5'-C*U*C*d(TCGCACCC)A*U*C*d(TCTCTCC)U*U*C*d(T)-3' |
| 6 | 5'-C*U*C*d(TCGCACCC)A*U*C*d(TCTCTCC)U*U*C*d(T)-3' |
| 7 | 5'-d(CTCTCGCACCCATCTCTCTCCTTCT)-3' |
| 8 | 5'-d(CTCTCGCACCCATCTCTCTCCTTCT)-3' |

Target Sequences

9    RNA    5'-GGAGGCU<u>AGAAGGAGAGAGAUGGGUGCGAGAG</u>CGU-3'
10    DNA    5'-d(CTU<u>AGAAGGAGAGAGATGGGTGCGAGAG</u>)-3'

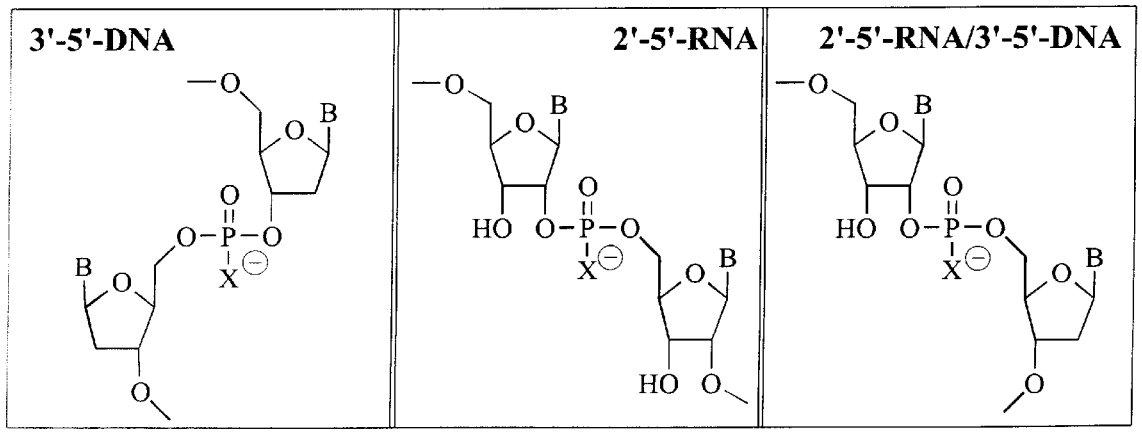

FIG. 1

MIXED BACKBONE ANTISENSE OLIGONUCLEOTIDES CONTAINING 2'-5'-RIBONUCLEOTIDE- AND 3'-5'-DEOXYRIBONUCLEOTIDES SEGMENTS

BACKGROUND OF THE INVENTION

1. Field of the Invention

This invention relates to the field of modified antisense oligonucleotides for in vitro and in vivo research, diagnostic, and therapeutic purposes.

2. Summary of the Related Art

Since Zamecnik and Stephenson (*Proc. Natl. Acad. Sci. USA* 75, 280 (1978)) first demonstrated virus replication inhibition by synthetic oligonucleotides, great interest has been generated in oligonucleotides as research, diagnostic, and therapeutic agents. In recent years the development of oligonucleotides as therapeutic agents and as agents of gene expression modulation has gained great momentum. The greatest development has been in the use of so-called antisense oligonucleotides, which form Watson-Crick duplexes with target mRNAs. Agrawal (*Trends in Biotechnology* 10, 152 (1992)) extensively reviews the development of antisense oligonucleotides as antiviral agents.

Great strides have been made in the development of antisense oligonucleotides for a variety of purposes. The use of antisense oligonucleotides as useful research tools to modulate gene expression is manifested, for example, by Holt et al. (*Mol. Cell Biol.* 8, 963 (1988)), who employed an antisense oligomer to inhibit HL-60 c-myc expression in order to study the role of a nuclear protooncogene in the regulation of cell growth and differentiation.

Other studies have demonstrated the utility of antisense oligonucleotides for research and therapeutic use. *Antisense Therapeutics* (S. Agrawal, Ed., Humana Press, Totowa, N.J., 1996); Thoung and Helene, *Angew. Chem. Int. Ed. Eng.* 32, 666 (1993); and *Antisense Research and Applications* (Crooke and Lebleu, Eds., CRC Press, Boca Raton, Fla., 1993).

Rapid degradation of "natural" phosphodiester backbone oligonucleotides by cellular nucleases (Sands et al., *Mol. Pharmacol.* 45, 932 (1994); Agrawal et al., *Clin. Pharmacokinet.* 28, 7 (1995)) necessitated chemical modifications of the phosphodiester backbone. Agrawal and Iyer (*Current Opin. Biotech.* 6, 12 (1995)) review a number of these approaches. See also Uhlmann and Peyman (*Chem. Rev.* 90, 543 (1990)). Several chemically modified oligonucleotides such as methylphosphonate (Smith et al., *Proc. Natl. Acad. Sci. USA* 83, 2787–2791 (1986); Sarin et al., *Proc. Natl. Acad. Sci. USA* 85, 7448–7451 (1988); Matsukura et al., *Proc. Natl. Acad. Sci. USA* 84, 7706–7710 (1987)), phosphorothioate (Id.), and phosphoramidate (Agrawal et al., *Proc. Natl. Acad. Sci. USA* 85, 7079–7083 (1988)) oligonucleotides show higher stability against nucleases. Many of these modifications have been tested against several disease targets in vitro and in vivo. (Agrawal, *Trends in Biotech.*, supra.; Agrawal and Iyer, *Curr. Opn. Biotech.* 6, 12–19 (1995)) Barker et al. (*Proc. Natl. Acad. Sci. USA* 93, 514 (1996)), for example, demonstrated successful inhibition of several genes of *Plasmodium falciparum* (which is responsible for malaria) in whole cell erythrocytes. They found that phosphorothioate antisense oligonucleotides can and do enter parasitized erythrocytes and inhibit expression of a number of genes essential to the reproduction and growth of the parasite.

Offensperger et al. (*EMBO J.* 12, 1257 (1993)) demonstrated complete inhibition of duck hepatitis B virus (DHBV) in DHBV-infected Peking ducks in vivo.

Simons et al. (*Nature* 359, 67 (1992)) reported that a phosphorothioate antisense c-myb 18-mer locally delivered to a rat with an injured left common carotid artery suppressed c-myb mRNA concentrations 2 weeks after injury and blocked the accumulation of intimal smooth muscle cells.

Ratajczak et al. (*Proc. Natl. Acad. Sci. U.S.A.* 89, 11823 (1992)) reported that 24-mer phosphorothioate oligonucleotides targeted to the human c-myb mRNA were infused, through a mini-osmotic pump, into scid mice bearing the human K562 chromic myeloid leukemia cell line. Mean survival times of the mice treated with the antisense oligonucleotide were six- to eightfold longer than those of mice untreated or treated with the sense controls.

Kitajima et al. (*Science* 258, 1792 (1992)) reported that after injecting IP 3'-phosphorothioate modified phosphodiester chimeric oligonucleotides that were complementary to the initiation codon region of the NF-κB mRNA (p65), they observed complete tumor involution in 13 out of 13 antisense-treated transgenic mice having that gene. Untreated or sense-treated mice died by 12 weeks, whereas the treated animals had no recurrence for at least 5 months.

Nesterova and Cho-Chung (*Nature Medicine* 1, 528 (1995)) reported in vivo tumor growth suppression in nude mice bearing LS-174T human colon carcinoma with antisense oligonucleotides targeted to the $RI_{60}$, subunit of cAMP-dependent protein kinase type I nucleic acid.

The phosphorothioate oligonucleotides advanced to human clinical trials because of their desirable properties observed in in vitro and in vivo studies. (Zhang et al., *Clin. Pharmacol. Ther.* 58, 44–53 (1995); Crooke et al., *Clin. Pharmacol. Ther.* 56, 641–646 (1994); Bayever et al., *Antisense Res. Dev.* 3, 383–390 (1993)). In order to improve pharmacokinetic properties of antisense phosphorothioate oligodeoxyribonucleotides, mixed backbone oligonucleotides (MBOs) have been designed that contain at least two different chemical modifications. Recent studies on MBOs such as hybrids, chimeras, etc., suggest that MBOs have improved pharmacokinetic properties and reduced toxicity with retention of comparable efficacy to phosphorothioate oligodeoxyribonucleotides. Zhang et al., *Biochem. Pharmacol.* 50, 545 (1995).

Most of the modifications currently explored for antisense purposes use the commonly occurring 3'-5' internucleotide linkage. In addition to the predominant 3'-5' internucleotide linkage, a less abundant 2'-5'-internucleotide linkage is formed in cells treated with interferon (Kerr and Brown, *Proc. Natl. Acad. Sci. USA* 75, 256 (1978); Lesiak et al., *J Biol. Chem.* 258, 13082 (1983)) and during intron splicing (Padget et al., *Science* 225, 898 (1984)).

Michelson and Monny (*Biochim. Biophys. Acta* 149, 107 (1967)) demonstrated that short 2'-5'-oligoadenylates form stable complexes with poly rU, although with lower $T_m$'s than their 3'-5' counterparts. Ts'o et al. (*Biochem.* 8, 997 (1969)), Tazawa et al. (*Biochem.* 8, 3499 (1970)), and Kondo et al. (*Biochem.* 9, 3479 (1970)) studied 2'-5'-linked r(ApA) and its binding to poly rU. Westheirner (*Acc. Chem. Res.* 1, 70 (1968)) demonstrated stability of 2'-5'-dimers and trimers to a few hydrolytic nucleases. Although the formation of 2'-5'-linkage is preferred over a 3'-5'-linkage under simulated prebiotic conditions (22,23), nature's selection of the 3'-5'-linkage over the 2'-5'-linkage to preserve genetic material has long been debated. Hashimoto and Switzer, *J. Am. Chem. Soc.* 114, 6255–6256 (1992); Jin et al., *Proc. Natl. Acad. Sci. USA* 90, 10568–10572 (1993); Usher and McHale, *Proc. Natl. Acad. Sci. USA* 73, 1149–1153 (1976).

More recently, Dougherty et al. (*J. Am. Chem. Soc.* 114, 6254 (1992)) and Hashimoto and Switzer (*J. Am. Chem. Soc.* 114, 6255 (1992)) reported preparation and hybridization properties of 2'–5'-DNA. Kierzek et al. (*Nucleic Acids Res.* 20, 1685 (1992)) presented a similar study of 2'–5 '-RNA. None of the foregoing studies were directed to antisense applications, however, as binding to 3'–5' RNA or DNA was not considered.

The utility of 2'–5'-linked oligonucleotides for antisense use has not been explored extensively, although a possible application has been suggested. Giannaris and Damha (*Nucleic Acids Res.* 21, 4742 (1993)) studied the hybridization characteristics of 2'–5'-RNA and hybrids of 2'–5'-RNA and 3'–5'-RNA with natural (i. e., 3'–5') single-stranded RNA and DNA. They found that introduction of 2'–5' internucleotide linkages decreases the $T_m$ of the duplexes formed between the 2'–5'-linkage-containing oligonucleotide and its target. They also observed that the 2'–5'-linkage-containing oligonucleotide selectively hybridized to RNA targets over DNA targets.

Seki et al. (*Nucleic Acids Symp. Series* 29, 71 (1993)) and Sawai et al. (*J. Biomol. Structure Dyn.* 13, 104 (1996)) reported on the hybridization affinities of 2'–5 '-linked oligo(rA) and oligo(rU) to each other and to 3'–5'-linked oligo(rA) and oligo(rU). They observed that a mixture of 2'–5' oligo(rA) and oligo(rU) formed double and triple helices in the same manner as a mixture 3'–5'-linked oligo (rA) and oligo(rU), but with lower $T_m$. The mixture of 2'–5'-linked oligo(rA) and oligo(rU) formed only a duplex at a much lower $T_m$. Thermodynamic studies showed that 3'–5'-linked oligoRNA possess more favorable base stacking and base pairing interactions compared to 2'–5'-linked RNA.

Alul (U.S. Pat. No. 5,532,130) disclosed 2'–5'-linked oligonucleotide-3'-deoxyribonucleotides for hybridizing to complementary RNA. They observed that such oligonucleotides selectively hybridize to RNA rather than DNA.

Despite the advances made, however, there is still a continuing interest in developing new and useful modifications to improve antisense oligonucleotide efficacy.

SUMMARY OF THE INVENTION

The present invention provides a new type of oligonucleotide for antisense applications. The oligonucleotides of the invention are mixed backbone oligonucleotides (MBOs) comprising both 2'–5'-RNA and 3'–5'-DNA. These oligonucleotides differ from prior art oligonucleotides, which do not have the combination of 2'–5'-RNA and 3'–5'-DNA. It has been surprisingly found that incorporating at least one 2'–5'-RNA linkage with at least one 3'–5'-DNA linkage in a single antisense oligonucleotide leads to several advantages. The oligonucleotides of the invention manifest higher stability against various exonucleases, including snake venom phosphodiesterase, S1 nuclease, and fetal calf serum. In addition, the presence of 2'–5' linkages results in oligonucleotides having diminished immune stimulation and significantly reduced effect on both complement and coagulation as compared to 3'–5' oligonucleotides. These results correlate with lower protein binding affinity of the inventive oligonucleotides as compared to natural 3'–5' oligonucleotides.

While they may be of any suitable length, oligonucleotides of the invention comprise about 12–50 nucleotides, of which at least two are ribonucleotides connected via a 2'–5' linkage and the remainder are 3'–5'-linked deoxyribonucleotides. The 2'–5'-linked ribonucleotides are connected to the 3'–5 '-linked deoxyribonucleotides by 3'–5'linkages.

Other than the foregoing, the oligonucleotides of the invention may also comprise one or more of any other modification that may be desirable. Many such modification are known in the art and include modifications to the nucleotide base and sugar groups (e.g., 2'-O-methylation) as well as modifications to the internucleotide linkage (e.g., phosphorothioate, phosphorodithioate, alkyl-(particularly methyl) and aryl-phosphonate and phosphonothioate, carbamate, etc.).

The oligonucleotides of the invention can be synthesized using known techniques and are useful for a variety of art recognized purposes. They are useful as tools for the selective inhibition of gene expression in vitro to study the role that the targeted gene plays in metabolic and/or reproductive processes. This is an attractive alternative to the laborious method of deletion mutation. Oligonucleotides according to the invention are also useful for inhibition of gene expression in vivo.

The foregoing merely summarizes certain aspects of the present invention and is not intended, nor should it be construed, as limiting the invention in any way. All patents and other publications recited herein are hereby incorporated by reference in their entirety.

BRIEF DESCRIPTION OF THE DRAWINGS

FIG. 1 displays the MBOs (rectangular segments below each target indicates which segment's linkages are phosphodiester (white rectangles) and which segment's linkages are phosphorothioate (black rectangles)), targets (underlined nucleotides represent those to which the MBOs are complementary), and the chemical structure of the internucleotide linkages.

DETAILED DESCRIPTION OF THE PREFERRED EMBODIMENTS

Figure 2A:
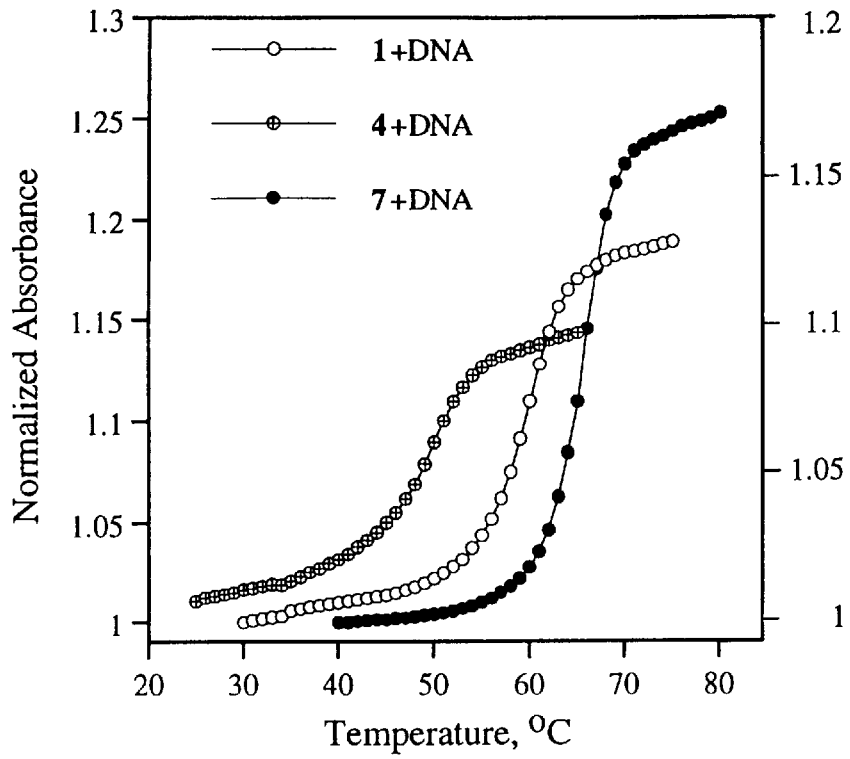
FIG. 2 displays two sets of melting curves, FIG. 2A being that for SEQ ID NOs 1, 4, and with complementary DNA, and FIG. 2B being that for SEQ ID NOs 3, 6, and 8 with complementary RNA.

The present invention comprises a novel class of oligonucleotides useful as antisense agents, both in vitro and in vivo. Oligonucleotides according to the invention comprise a sequence having at least two ribonucleotides connected by a 2'–5' internucleotide linkage with the remaining nucleotides being deoxyribonucleotides connected to the 2'–5' interconnected ribonucleotides and to each other by 3'–5' internucleotide linkages. Thus, the oligonucleotides of the invention comprise both RNA and DNA.

As demonstrated herein, MBOs containing 2'–5'-ribonucleotides and 3'–5'-deoxyribonucleotides bind to both DNA and RNA target strands. Although, 2'–5' RNA generally binds with lower affinity to its target, the oligonucleotides of the invention manifest higher stability against various exonucleases, including snake venom phosphodiesterase, S1 nuclease, and fetal calf serum. In addition, the presence of 2'–5' linkages results in the inventive oligonucleotides having diminished immune stimulation and significantly reduced effect on both complement and coagulation as compared to 3'–5'-linked oligonucleotides. These results correlate with lower protein binding affinity of the inventive oligonucleotides as compared to natural 3'–5' oligonucleotides.

"Natural" 3'–5 '-inked oligonucleotides exist predominantly in C2'-endo and C3'-endo sugar conformations. Saenger, in *Principles of nucleic Acid Structure*, Ch. 9 (Springer, New York, 1984). The C2'-endo sugar conformation exists exclusively in DNA, giving it an extended B-type structure, while the C3'-endo sugar conformation occurs in both RNA and DNA nucleotides, giving them a compact A-type structure when bound to RNA and DNA duplexes. Id. A recent molecular modeling study predicted that the C2'-endo sugar conformation is predominant in 2'–5'-RNA and C3'-endo sugar conformation exists in 2'–5'-DNA. Lalitha and Yathindra, *Current Sciences* 68, 68 (1995). These conformations are exactly the opposite of what is observed with 3'–5'-RNA and DNA. Although the invention is not limited by any theory, we theorize that MBOs with a limited number of 2'–5'-ribonucleosides within a 3'–5' deoxyribonucleotide core bind efficiently to the "natural" DNA and RNA complementary strands, since such MBOs possess uniform intra-phosphate distances throughout the oligonucleotide chain.

The number of 2'–5'-linked ribonucleotides in the oligonucleotides according to the invention will vary as a function of the length of the oligonucleotide, owing to the fact that the presence of one or more 2'–5'-linked ribonucleotides generally results in a decreased binding affinity for the target. Oligonucleotides according to the invention will have a sufficient number of such linkages to confer exonuclease resistance on the oligonucleotide. Because exonucleolytic degradation occurs primarily from the 3' end in vivo, the oligonucleotides of the invention preferably have at least two 2'–5'-linked ribonucleotides at the 3' end of the oligonucleotide or one nucleotide from the 3' end.

In another preferred embodiment, oligonucleotides according to the invention have two or more 2'–5'-linked ribonucleotides in the middle of the oligonucleotide. For the purposes of this invention, the "middle" is defined as that region of the oligonucleotide comprising other than the four 3' and 5' terminal nucleotides. In other words, in this embodiment, oligonucleotides have at least two 2'–5 '-linked ribonucleotides that are at least four or more nucleotides from both the 3' and 5' termini of the oligonucleotide. Oligonucleotides according to this aspect of the invention have improved pharmacokinetic properties.

The number of 2'–5'-linked ribonucleotides can vary from two to all but two of the oligonucleotides' nucleotides (i.e., the oligonucleotides of the invention will have at least two deoxyribonucleotides). The relative number of 2'–5' ribonucleotides and 3'–5' deoxyribonucleotides will depend on the particular application, but in any event it is routine matter for those skilled in the art using known techniques and those disclosed herein to determine a suitable number.

Oligonucleotides according to the invention can be of any length for a desired application. Preferably, oligonucleotides according to the invention are from about 12 to about 50 nucleotides long and most preferably from about 20 to about 35 nucleotides long.

In addition to the foregoing, the oligonucleotides of the invention can include any modification that is desirable for an intended application. Many such modifications are known to those skilled in the art. See, e.g., Agrawal and Iyer (supra) and Uhlmann and Peyman (supra). While generally the nucleotide base is selected from the naturally occurring ones (i.e., A, U, T, G, and C), modified nucleotide bases can also be used. Similarly, oligonucleotides according to the invention can have one or more modified internucleotide linkages, such as, but not limited to phosphorothioates, phosphorodithioates, alkyl- (particularly methyl) and aryl-phosphonates, phosphoramidates, carbamates, etc. Preferably, oligonucleotides according to the invention will have one or more 2'–5' and/or 3'–5' phosphorothioate linkages. The nucleotide sugar moiety may also be modified, such as with a substituent (particularly O-methyl) at the 2' position (for nucleotides with a 3' linkage) or at the 3' position (for nucleotides with a 2' linkage). It will be appreciated that one or more of the same or different of any of the foregoing modifications can be employed in the a oligonucleotides according to the invention. Generally, these modifications will be chosen for the purposes of increasing the oligonucleotide's efficacy at inhibiting target nucleic acid expression and improving pharmacokinetic safety profiles. Thus, the modifications can be incorporated, for example, to increase resistance to nucleolytic degradation, to enhance cellular uptake, to increase target hybridization affinity, and/or induce RNase H action.

In addition, oligonucleotides according to the invention can be constructed to have a variety secondary structures. Such structures can be those found in self-stabilized oligonucleotides (WO94/01550), foldback triplex-forming oligonucleotides (WO94/17091), and branched oligonucleotides (WO95/32986).

Oligonucleotides according to the invention can be synthesized according to standard techniques. E.g., *Methods in Molecular Biology*, Vol 20, *Protocols for Oligonucleotides and Analogs* (Agrawal, Ed., Humana Press, Totowa, N.J., 1993); *Methods in Molecular Biology*, Vol 26, *Protocols for Oligonucleotide Conjugates* (Agrawal, Ed., Humana Press, Totowa, N.J., 1994). Where a 2'–5' linkage is desired, one can use, for example, a suitably 3' protected nucleotide monomer (such as a 3'-t-butylmethylsilyl-2'-β-cyanoethyl phosphoramidite monomer) at the appropriate point in the stepwise synthesis.

Oligonucleotides according to the invention can have any desired sequence. For antisense purposes, for example, an oligonucleotide according to the invention will have at least a portion of its sequence complementary to a nucleic acid whose expression is desired to be inhibited. Such a nucleic acid can be endogenous to a cell. The endogenous nucleic acid can be naturally occurring, a mutation of a naturally occurring nucleic acid, or a non-naturally occurring nucleic acid whose expression inhibition is desired for research purposes, such as to determine the role of the nucleic acid in biological processes. In such an instance, oligonucleotides according to the invention are useful research tools to study role of the nucleic acid by selective inhibition of the endogenous nucleic acid's expression, either in vitro or in vivo. Alternatively, the endogenous nucleic acid can be a mutant whose aberrant expression results in (either directly or indirectly) a diseased state and, therefore, whose expression inhibition is also desired for therapeutic purposes.

Similarly, the target nucleic acid can be exogenous to the cell or organism, such as in the case of viral nucleic acids (e.g., HIV) and other pathogens (e.g., *P. falciparum*) that has infected the cell. In these instances, at least a portion of the oligonucleotides according to the invention is complementary to a nucleic acid essential to the metabolism, growth, or reproduction of the virus or other pathogen and whose expression inhibition results in partial or full, temporary or permanent alleviation of the effects of the infection. Such oligonucleotides are also useful both in vitro and in vivo.

In view of the foregoing, therefore, methods of nucleic acid expression inhibition using the oligonucleotides disclosed herein are also part of the invention. Such methods include contacting a target nucleic acid with an oligonucleotide according to the invention (either in vitro or in vivo) under conditions suitable for hybridization, thereby causing the target nucleic acid's expression to be inhibited. For the purposes of the invention, the phrase "contacting a target nucleic acid with an oligonucleotide according to the invention" includes, unless otherwise expressly stated or restricted, all actions a direct result of which is that the oligonucleotide according to the invention to come in contact with the target nucleic acid. Thus, it includes, for example, adding a solution containing an oligonucleotide of the invention to a solution containing the target nucleic acid as well as administering the oligonucleotide to a subject whose cells contain the target nucleic acid.

As is evident, the present invention contemplates administration of an oligonucleotide according to the invention to an animal (preferably a mammal; most preferably a human) suffering from a disease, infection, or other abnormality resulting from expression of a nucleic acid not normally expressed in the healthy animal (such as endogenous and exogenous target nucleic acids discussed above). Administration can be by any suitable technique that brings the oligonucleotide into contact with the nucleic acid whose expression inhibition is desired. Administration can be by art recognized techniques or routine modifications of them. E.g., Agrawal et al., *Biochem. Pharmacol.* 50, 571 (1995); Zhang et al., *Biochem. Pharmacol.*, supra.

The following Examples are presented for illustrative purposes only and are not intended, nor should they be construed, as limiting the invention in any way. Those skilled in the art will appreciate that variations can be made without violating the spirit or scope of the invention.

EXAMPLES

Example 1

Synthesis and Purification of Oligonucleotides

Oligonucleotide sequences synthesized as described below are shown in FIG. 1. Oligonucleotides SEQ ID NOs 1–3 contain three 2'–5'-linkages at each of the 5'- and 3'-ends. Oligonucleotides SEQ ID NOs 4–6 contain three 2'–5' linkages at each of the ends, and an additional three 2'–5'-linkages in the middle as shown in FIG. 1. Oligonucleotides SEQ ID NOs 7 and 8 are control oligonucleotides containing all 3'–5' linkages. The target oligonucleotides SEQ ID NOs 9 and 10 contain a 25 base long sequence (5'-AGAAGGAGAGAGAUGGGUGCGAGAG-3'; SEQ ID NO 11) (underlined in SEQ ID NOs 9 and 10 in FIG. 1) from the initiation codon region of the HIV-1 gag mRNA. A phosphorothioate oligonucleotide complementary to this site has been studied extensively for therapeutic efficacy, toxicological and pharmacokinetic properties (Zhang et al., *Clin. Pharmacol.* Ther., supra) and is currently in human clinical trials.

Oligonucleotides were synthesized on a Milligen (Bedford, Mass.) 8700 DNA synthesizer on a 1 $\mu$M scale using phosphoramidite chemistry. Beaucage, In *Methods in Molecular Biology*, Vol. 20, *Oligonucleotides and Analogs*, pp. 33–62, S. Agrawal, ed., Humana Press, Totowa, N.J.,) $\beta$-cyanoethyl phosphoramidite monomers were obtained from Millipore (Bedford, Mass.) and Pharmacia (Piscataway, N.J.). 3'-t-Butyldimethylsilyl-2'-$\beta$-cyanoethyl phosphoramidite and 2'-t-butyldimethylsilyl-3'-$\beta$-cyanoethyl phosphoramidite monomers were used for 2'–5' and 3'–5'-RNA synthesis, respectively. After synthesizing the oligonucleotides, the CPG was treated with concentrated ammonium hydroxide at room temperature for 2 hours, and then the supernatant was heated at 55° C. for 6 hours for the control 3'–5' oligodeoxyribonucleotides. The oligonucleotides with 5'-DMT group were purified on a Waters (Milford, Mass.) 650 HPLC system using 0–50% gradient of 0.1M ammonium acetate and 80% acetonitrile containing 0.1M ammonium acetate using a $C_{18}$ reverse phase column. The appropriate peak was collected, concentrated, and treated with 80% acetic acid at room temperature for 1 hr to remove the 5'-DMT group. The oligonucleotides were desalted on Waters $C_{18}$ Sep-pack cartridges and quantified by measuring absorbance at 260 nm using extinction coefficients, which were calculated by the nearest neighbor method (Puglisi and Tinoco, In *Methods in Enzymology*, Dahlberg and Abelson, eds., Volume 180, Academic Press, San Diego, Calif., pp. 304–325 (1989)) after ascertaining the purity by PAGE.

MBOs and the target oligoribonucleotide (RNA) were deprotected with a 3:1 mixture of ammonium hydroxide and ethanol at 55 ° C. for about 15 hrs and then with 1M tetrabutylammonium fluoride at room temperature for another 15 hrs. MBOs and normal RNA were then purified on 20% denaturing PAGE, eluted from the gel, and desalted using $C_{18}$ Sep-pack cartridges (Waters). Incorporation of 2'–5'-linkages and base composition were confirmed by nuclease digestion of oligonucleotides and HPLC identification of the hydrolysis products (Giannaris and Damha, supra).

Example 2

Thermal Melting Studies

Thermal denaturation studies were carried out by mixing MBOs with the DNA or RNA target strands in equimolar ratios in 10 mM disodium hydrogen phosphate, pH 7.5±0.1, 100 mM sodium chloride buffer, heated to 95° C. for 10 min, and allowed to come to room temperature slowly before being stored at 4° C. overnight. The final total concentration of the oligonucleotide strands was 2.0 $\mu$M. Spectrophotometric measurements were performed at 260 nm using 1 cm path length quartz cuvettes at a heating rate of 0.5° C./min on a Perkin-Elmer (Norwalk, Conn.) Lambda 2 Specotrometer attached to a thermal controller and a personal computer. Melting temperatures ($T_m$) taken as the temperature of half-dissociation and were obtained from first derivative plots. Precision in $T_m$ values estimated from variance in two or three repeated experiments was ±0.5° C. The results are displayed in FIG. 2 and in Table 1.

TABLE 1

| SEQ. ID. NO. | $T_m$ (°C.) DNA | $T_m$ (°C.) RNA | HIV-1 Inhibition $IC_{50}$ (nM) | Stimulation Index (Lymphocyte Proliferation) (at 10 µg/ml) | 50% Prolongation of Clotting (aPTT) (µg/ml) | 50% Inhibition of Complement Lysis (µg/ml) |
|---|---|---|---|---|---|---|
| 1 | 60.6 | 67.8 | nd | 0.67 ± 0.11 | >>100.0 | nd |
| 2 | 52.5 | 63.3 | 99.9 | 2.82 ± 0.37 | 51.1 | 59.1 |
| 3 | 51.9 | 61.1 | 29.8 | 4.93 ± 0.15 | 58.0 | 95.2 |
| 4 | 52.8 | 64.5 | nd | nd | >>100.0 | nd |
| 5 | 43.2 | 61.2 | 812.5 | 1.09 ± 0.05 | 115.0 | nd |
| 6 | 39.4 | 56.4 | nd | 0.23 ± 0.04 | 98.3 | >500.0 |
| 7 | 63.5 | 70.5 | nd | 1.10 ± 0.13 | >>100.0 | >500.0 |
| 8 | 56.6 | 63.5 | 24.9 | 6.16 ± 0.12 | 23.2 | 34.2 | nd: not determined

Figure 2B:
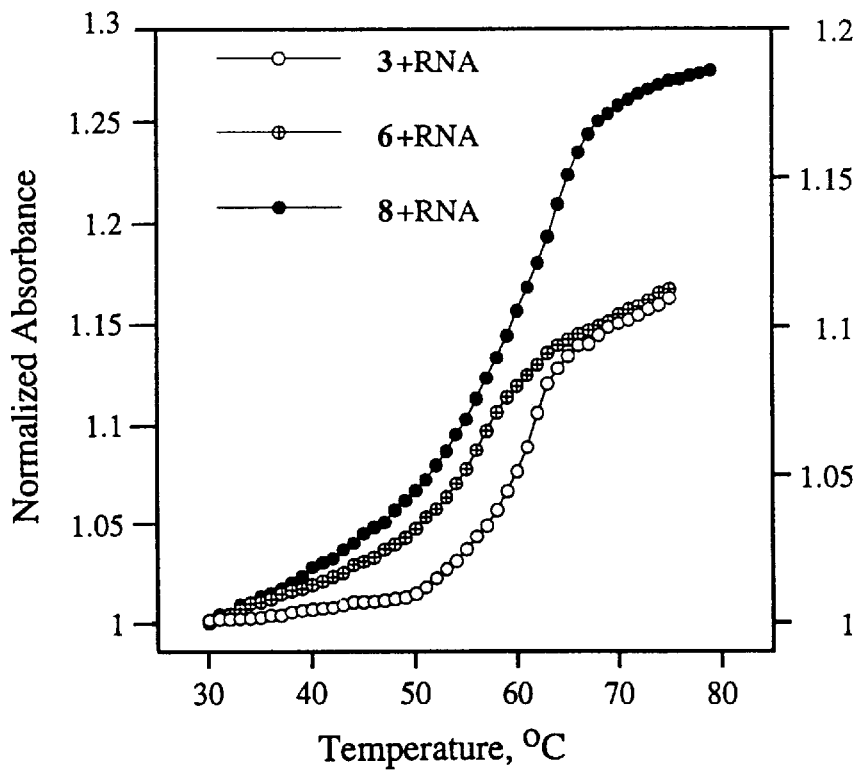

In general, sharp, cooperative and single transition melting curves were observed for all the oligonucleotides (FIG. 2A). Melting transitions were slightly broader with phosphorothioate analogs (FIG. 2), however. The duplexes of MBO SEQ ID NO 1 with the DNA SEQ ID NO 10 (FIG. 2A) and RNA SEQ ID NO 9 target strands showed $T_m$s of 60.6° C. and 67.8° C., respectively. That is about 2.9° and 2.7° C. lower, respectively, than the duplexes of the control oligonucleotide SEQ ID NO 7 with the same DNA and RNA target strands. The duplexes of oligonucleotide SEQ ID NO 4 containing three more 2'–5' linkages in the middle of the sequence) with the DNA SEQ. I.D. NO. 10 (FIG. 2A) and RNA SEQ ID NO 9 target strands had $T_m$s of 52.8° and 64.5° C., respectively. The presence of 2'–5'-linkages in the middle of the sequence showed higher destabilizing effect on the duplex with the DNA strand ($\Delta T_m$=-10.7° C.) than with the RNA strand ($\Delta T_m$=-6.0° C.). Similar results were observed with the duplexes of oligonucleotides SEQ ID NOs 2 and 5, which have 2'–5'-phosphodiester and 3'–5'-phosphorothioate linkages, respectively. The $T_m$s of the duplexes of oligonucleotides SEQ ID NOs 2 and 5 were 52.5° and 43.2° C. with the DNA strand SEQ ID NO 10, and 63.3° and 61.2° C. with the RNA strand SEQ ID NO 9, respectively.

Oligonucleotides SEQ ID NOs 3 and 6 are phosphorothioate analogs of SEQ ID NOs 1 and 4, respectively. Phosphorothioate analogs showed more interesting hybridization properties with the DNA and RNA strands than the phosphodiester analogs. The $T_m$s of the duplexes of oligonucleotide SEQ. I.D. NO. 3 with the DNA SEQ ID NO 10 and RNA SEQ ID NO 9 (FIG. 2B) target strands were 51.9° and 61.1° C., respectively. That is about 4.70°and 2.4° C. lower than the $T_m$s of the duplexes of control phosphorothioate oligonucleotide SEQ ID NO 8 with the DNA SEQ ID NO 10 and RNA SEQ ID NO 9 (FIG. 2B) target strands, respectively (Table 1). Similarly, oligonucleotide SEQ ID NO 6, with nine 2'–5' linkages, had 17.2° and 7.1 ° C. lower $T_m$s than duplexes of oligonucleotide SEQ ID NO 8 with the DNA SEQ ID NO 10 and RNA SEQ ID NO 9 target strands, respectively.

Comparison of the $T_m$s of the duplexes of phosphodiester and phosphorothioate oligonucleotides with the DNA SEQ ID NO 10 and RNA SEQ ID NO 9 strands suggests that 2'–5'-phosphorothioate linkages had a higher destabilizing effect on the duplex with the DNA SEQ ID NO 10 strand than the duplex with the RNA SEQ ID NO 9 strand.

Example 3

Circular Dichroism Studies

The same oligonucleotide sample solutions used for the UV thermal melting studies were used for CD experiments also. The CD spectra were recorded on a JASCO (Japan) J-710 Spectropolarimeter attached to a peltier thermal controller using a 0.5 cm quartz cell. The samples were equilibrated at the required temperature for 15 min before recording the spectra. Each spectrum was an average of eight scans subtracted with the buffer blank, which was also an average of eight scans and obtained at the same scan speed (100 nm/min). All the spectra were noise reduced using the software supplied by Jasco, Inc. and the molar ellipticities were calculated using the same software.

Figure 3A:
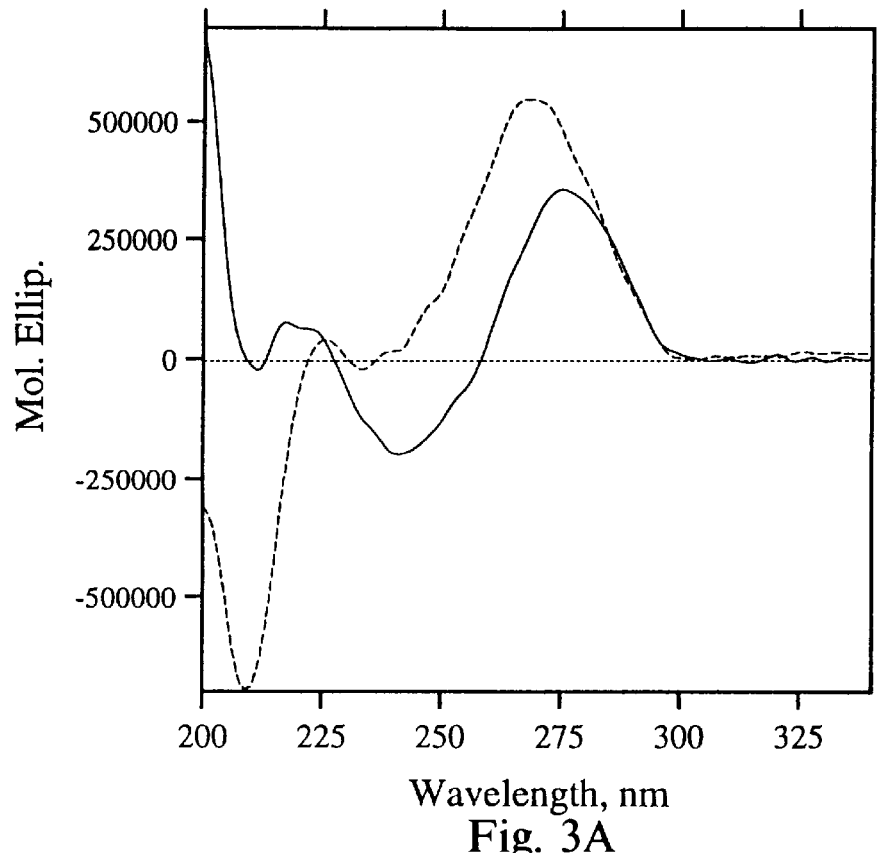
FIGS. 3A–C display circular dichroism spectra measured in Example 3.
Figure 3B:
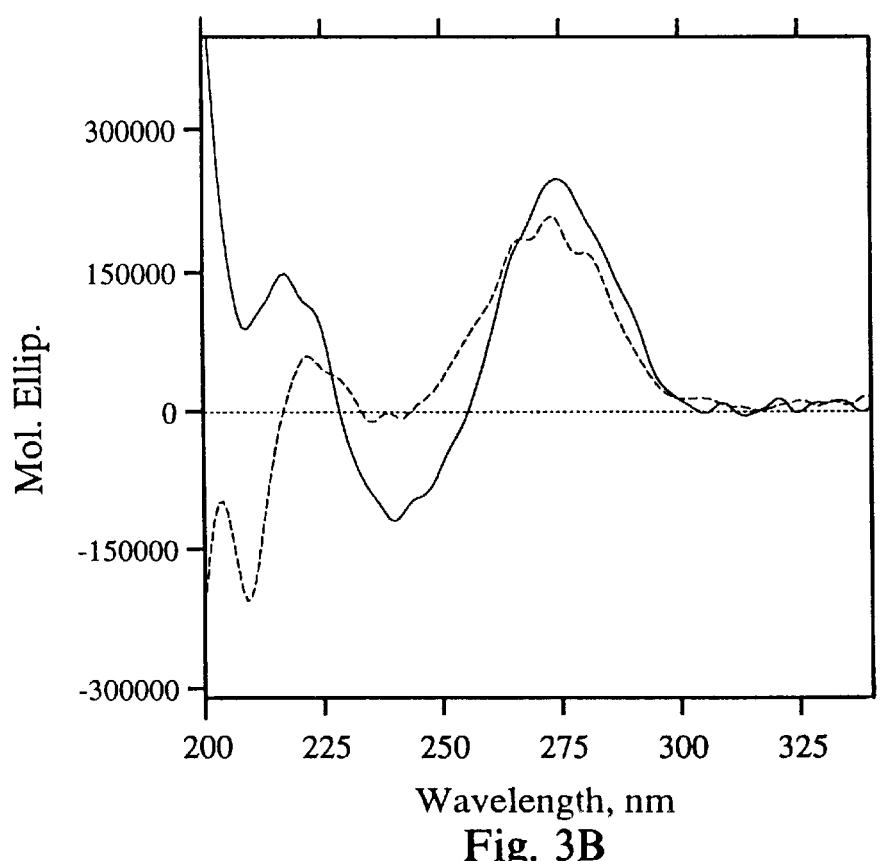
Figure 3C:
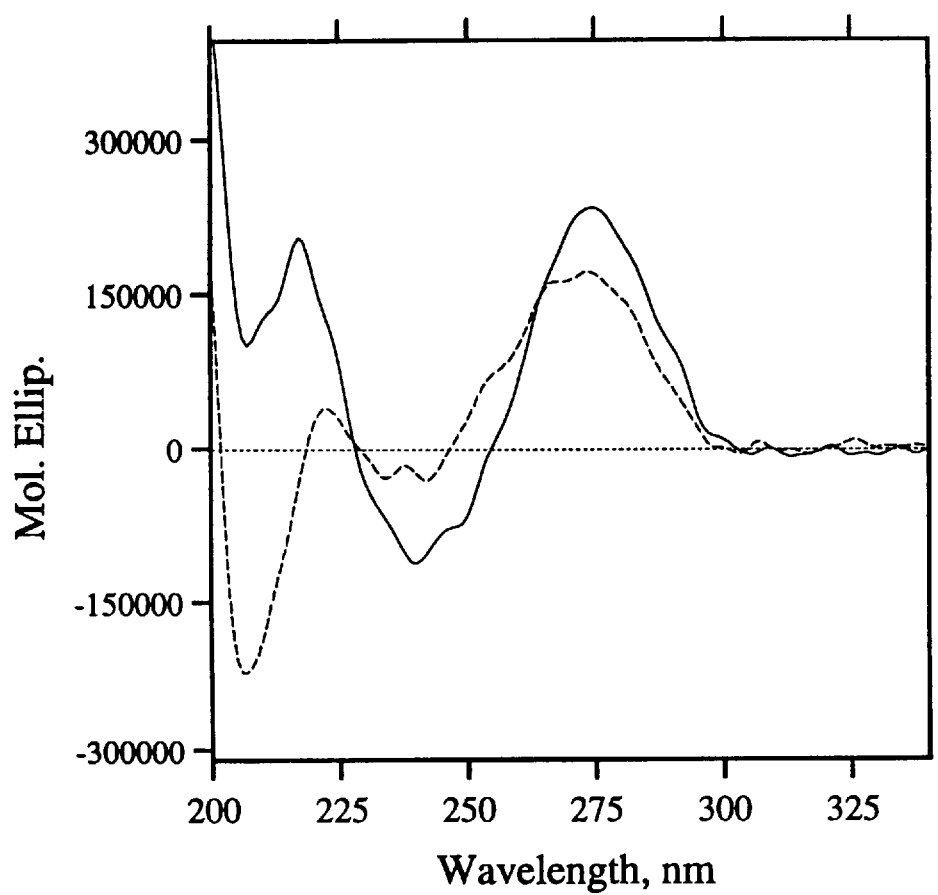

A representative set of CD spectra for phosphorothioate analogs (SEQ ID NOs 3, 6 and 8) are shown in FIG. 3. The duplexes of MBOs exhibited CD spectral characteristics similar to those of the duplexes of control oligonucleotides containing all 3'–5'-linkages. The ratios of the positive peak and the negative trough in the higher wavelength region (275 and 245 nm, respectively) of the CD spectra of the duplexes of MBOs with target strand suggests both B- and A- type (mixed) CD spectral characteristics, with pronounced B-type characteristics. Kandimalla et al., submitted (1996)) The duplexes of MBOs with the RNA target strand exhibited A-type of CD spectral characteristics similar to that of the control oligonucleotide SEQ ID NO 8 (FIG. 3). The higher wavelength positive band of the RNA duplexes of MBOs is centered around 274 nm, however, unlike in the case of control oligonucleotide duplex with the RNA strand (268 nm). The CD experimental results confirm that the MBOs (SEQ ID NOs 1–6) form ordered right handed double helical structures with both the complementary DNA SEQ ID NO 10 and RNA SEQ ID NO 9 complementary strands as in the case of control phosphodiester (SEQ ID NO 7) and phosphorothioate (SEQ ID NO 8) oligonucleotides.

Example 4

Gel Mobility Shift

Duplex formation by MBOs with both the DNA and RNA target strands was further confirmed by electrophoretic mobility shift assay. The DNA target strand SEQ ID NO 10 was labeled at the 5'-end with $^{32}P$ using $\gamma$-$^{32}P$-ATP (Amersham, Arlington Heights, Ill.) and T4 polynucleotide kinase (Promega, Madison, Wis.) (Sambrook et al., *Molecular Cloning*, Cold Spring Harbor Press, Cold Spring Harbor, N.Y. (1989)). The RNA target strand was labeled at the 3'-end using T4 RNA ligase (New England Biolabs, Beverly, Mass.) and [$^{32}P$]pCp (New England Nuclear, Boston, Mass.) using standard protocols. Id. A small amount of DNA SEQ ID NO 10 or RNA SEQ ID NO 9 target strand (~3000 cpm of labeled and 1 nM of cold) was mixed with different ratios of MBOs in 10 mM disodium hydrogen phosphate, pH 7.4–7.6, 100 mM sodium chloride buffer. The samples were heated at 95° C. for 15 min and allowed to come to room temperature before being stored at 4° C. overnight. The samples were loaded on a non-denaturing 10% polyacrylamide gel with glycerol dye. The gel was run at room temperature using tris/glycine buffer. After electrophoresis the autoradiogram was developed by exposing the dried gel to Kodak X-Omat AR film at −70° C. with an intensifying screen on.

Figure 4:
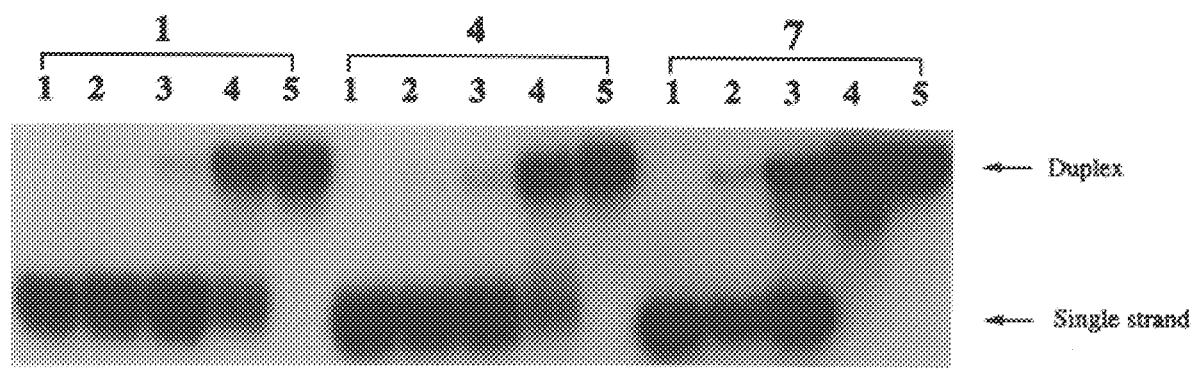
FIG. 4 displays autoradiograms from the gel mobility shift assay for the binding of control oligonucleotides and MBOs to the DNA target strand, as described in Example 4.

A representative gel for phosphodiester analogs (SEQ ID NOs 1, 4, and 7) with the DNA target strand SEQ ID NO 10 is shown in FIG. 4. The appearance of a slow moving band with increasing concentrations of oligonucleotides suggest formation of duplex structures with the DNA target strand. The absence of any other bands except the duplex band at higher ratios (1:2) also suggests that the new oligonucleotides form complexes with 1:1 stoichiometry, i.e., duplex structures only.

Example 5

Resistance to Nucleolytic Degradation

Oligonucleotides were labeled at the 5'-end with $^{32}P$ using $\gamma$-$^{32}P$-ATP (Amersham) and T4 polynucleotide kinase (Promega). Sambrook et al, *Molecular Cloning, supra*. Stability of the oligonucleotides in cell culture medium containing 10% fetal calf serum was tested by incubating a small amount of labeled oligonucleotide together with 100 ng of cold oligonucleotide in DMEM cell culture medium (Gibco/BRL, Grand Island, N.Y.) containing 10% non-heat-inactivated fetal calf serum (Gibco/BRL) at 37° C. in a final volume of 40 μl, and aliquots were removed at different times.

For snake venom phosphodiesterase assay, labeled oligonucleotide with cold oligonucleotide in a buffer (10 mM Tris, pH 8.0, 100 mM sodium chloride, and 10 mM magnesium chloride) was incubated with 0.01 U of snake venom phosphodiesterase (Boehringer-Mannheim, Indianapolis, Ind.) at 21° C. (final volume 40 μl). Aliquots were removed at different time intervals for electrophoretic gel analysis. For S1 nuclease assay, reactions were carried out as above but in 100 nM sodium acetate, pH 5.0, 10 mM zinc acetate buffer and with 1.4 U of S1 nuclease (Gibco/BRL) incubated at 37° C. in a final volume of 50 μl. Aliquots were removed at different time intervals for electrophoretic gel analysis. Nuclease reactions were stopped by adding 5 μl of formamide gel loading buffer to each sample and heating at 90° C. for 5 min. All the samples were then run by 20% PAGE (7M urea) and visualized by autoradiography.

Figure 6:
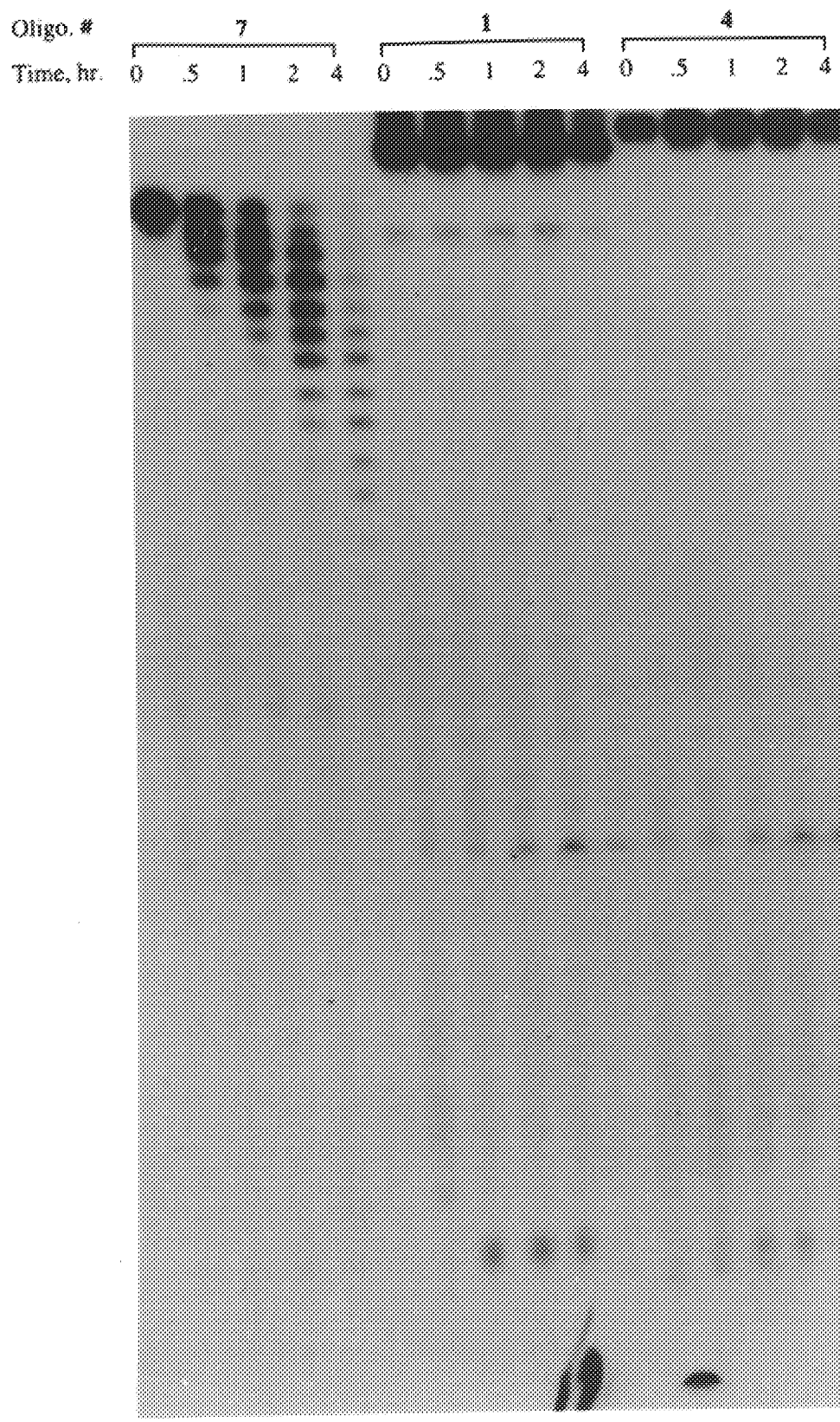
FIG. 6 displays an autoradiogram resulting from incubation for different times of phosphodiester analogs of control oligonucleotide SEQ. ID. NO. 7 and MBOs SEQ ID NOs 1 and 4 in DMEM cell culture medium containing 10% fetal calf serum.

Natural phosphodiester backbone oligonucleotides are digested in less than 5 min in vivo, making them unsuitable for therapeutic uses. Sands et al., *Mol. Pharmacol.* 45, 932–943 (1994); Agrawal, *Clin. Pharmacokinet.* 28, 7–16 (1995) Phosphorothioate analogs are considerably more stable in vivo. Agrawal et al., *Clin. Pharmacokinet.* 28, 7–16 (1995); Zhang et al., *Biochem. Phannacol.* 49, 929–939 (1995). Any modified oligonucleotide should show both reasonable stability against nucleases and acceptable hybridization properties with the target RNA to be useful as an antisense agent. FIG. 6 shows stability of phosphodiester analogs of MBOs and a control oligonucleotide. Oligonucleotide SEQ ID NO 7 was digested quickly in serum with a short half-life, <30 min (FIG. 6). This result is consistent with the reported data on phosphodiester oligonucleotides (Sands et al., *Mol. Pharmacol.*, supra). At the two hour time point only a faint band of intact oligonucleotide SEQ ID NO 7 was present. MBOs SEQ ID NOs 1 and 4 were intact up to four hours. Both the MBOs showed negligible digestion in this time period. These in vitro results suggest that 2'–5'-modification is more stable to serum nucleases than 3'–5'-linkage.

Figure 7A:
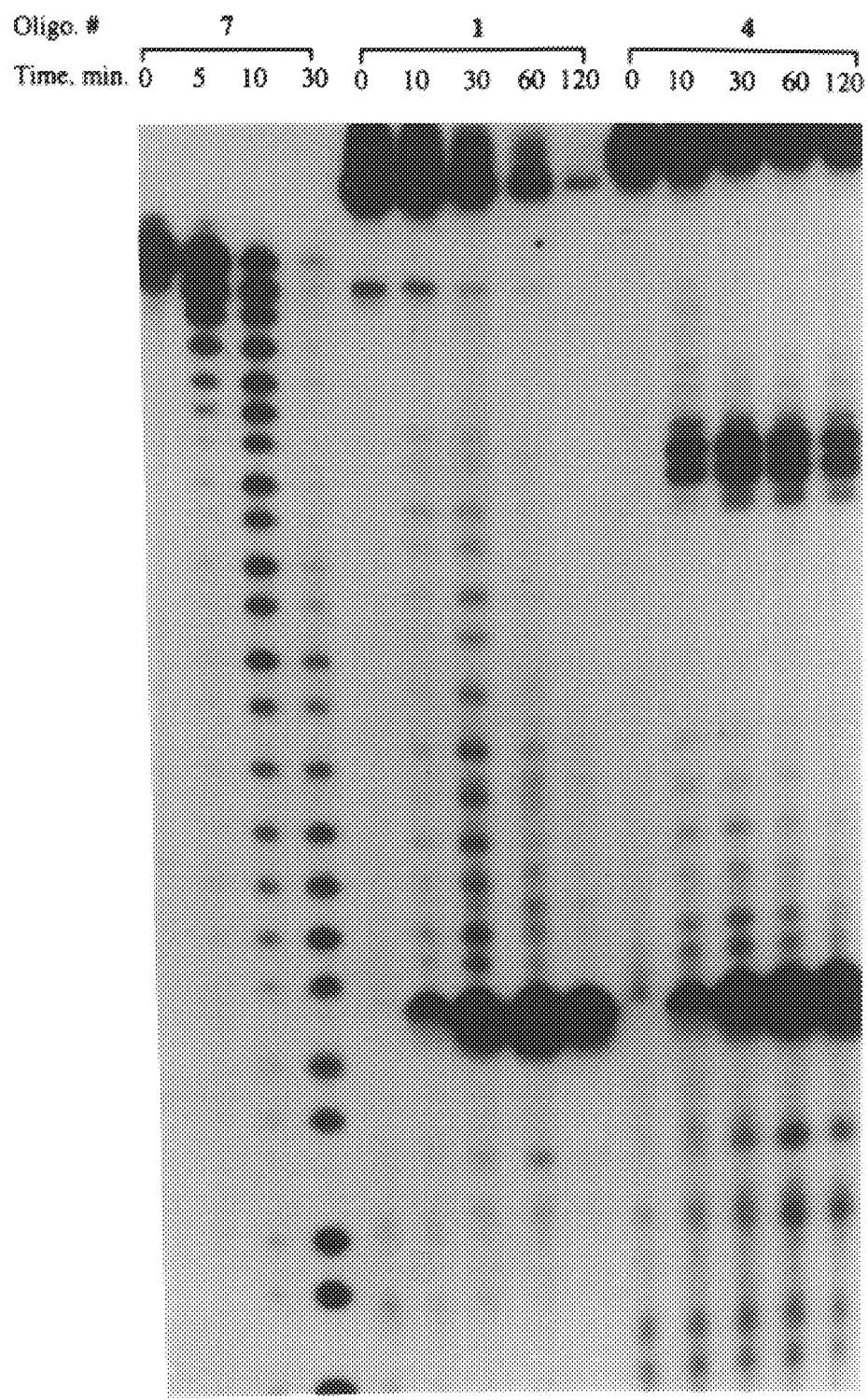
FIG. 7 displays an autoradiogram resulting from the incubation for different times of phosphodiester analogs of control oligonucleotide SEQ. ID. NO. 7 and MBOs SEQ ID NOs 1 and 4 against snake venom phosphodiesterase (FIG. 7A) and S1 nuclease (FIG. 7B).
Figure 7B:
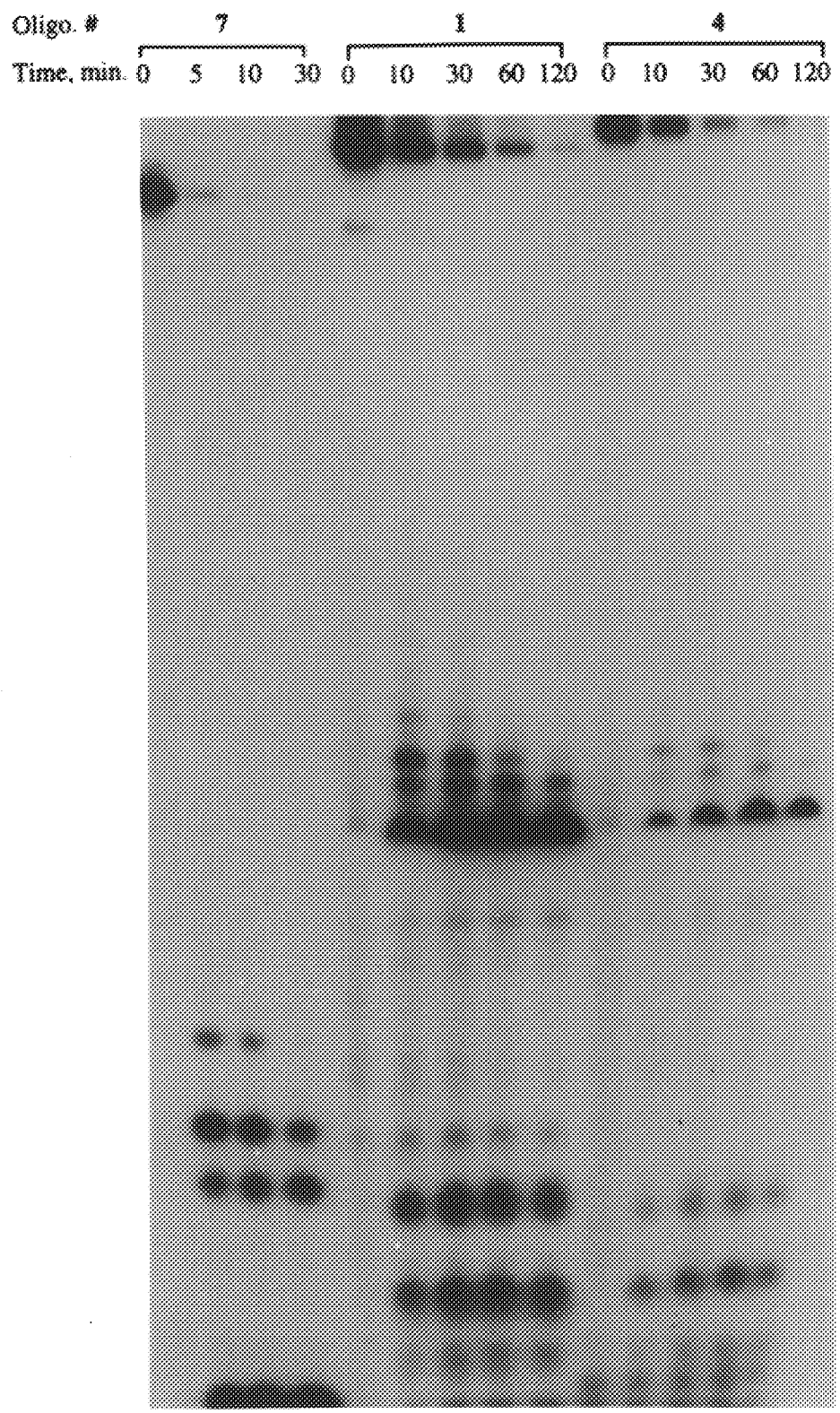

The studies with snake venom phosphodiesterase (3'-exonuclease) suggest slightly higher stability of oligonucleotides SEQ ID NOs 1 and 4 than SEQ ID NO 7 (FIG. 7A). Digestion of SEQ ID NOs 1 and 4 in the presence of snake venom phosphodiesterase is mainly due to slow endonucleolytic activity rather than exonucleolytic activity. In studies with S1 nuclease (an endonuclease), both SEQ ID NOs 1 and 4 were quickly digested as in the case of SEQ ID NO 7 (FIG. 7B). We infer from these results that phosphorothioate analogs of MBOs (SEQ ID NO 1 and 4) are more stable against nucleases.

Example 6

RNase H Activation

RNase H is an enzyme that selectively recognizes 3'–5'-DNA-RNA hetero-duplexes and hydrolyzes the RNA strand of the hetero-duplex. Cedergren and Grosjean, *Biochem. Cell. Biol.* 65, 677–692 (1987). RNase H possesses both endo- and 3'→5'-exonuclease activities. Schatz et al., *EMBO J.* 9, 1171–1176 (1990). RNase H requires a 4–6 bp hybrid duplex to elicit its activity on the target RNA strand. Agrawal et al., *Proc. Natl. Acad. Sci.* USA 87, 1401–1405 (1990). We investigated the RNase H activation properties of MBOs using the same 35-mer RNA target strand (SEQ ID NO 9) used for spectroscopic studies.

RNase H assays were performed as described earlier. Kandimalla et al., *Nucleic Acids Res.* 23, 3578–3584 (1995)) Briefly, a small amount of the 3'-end-labeled RNA, 90 pmol of yeast tRNA, and oligonucleotides under study were mixed in 30 μl of 20 mM Tris-HCl, pH 7.5, 10 mM $MgCl_2$, 10 mM KCl, 0.1 mM DTT, 5% w/v sucrose, and 40 U of RNasin (Promega) and incubated at room temperature for 30 min. An aliquot (7 μl) was removed as a control, and 0.8 U of *E. coli* RNase H (Boehringer-Mannheim) was added to the remaining reaction mixture. The reaction mixture with RNase H was incubated at room temperature, and aliquots (7 μl) were removed at different time intervals. The samples were analyzed on a 7M urea-20% polyacrylamide gel. After electrophoreses, the autoradiogram was developed by exposing the dried gel to Kodak X-Omat AR film at −70° C. with an intensifiing screen on.

Figure 5A:
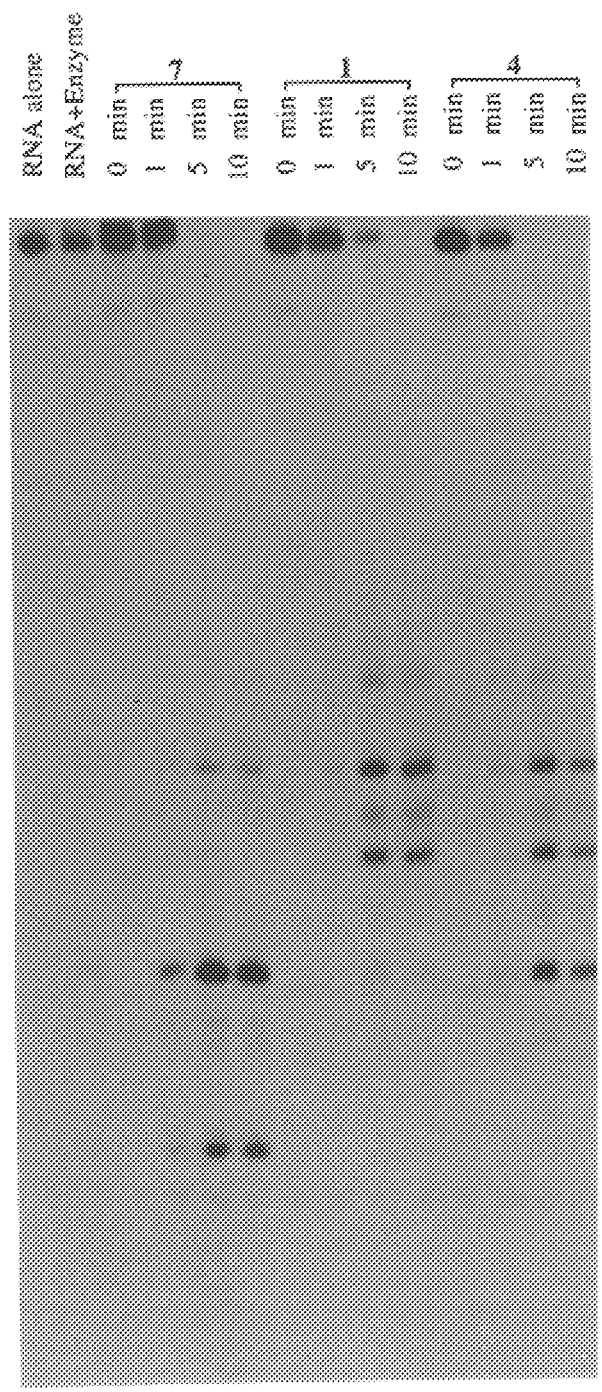
FIG. 5 displays an autoradiogram showing the RNase H hydrolysis pattern of the RNA target strand in the absence and presence of phosphodiester analogs of the control oligonucleotide SEQ. ID. NO. 7 and MBOs SEQ ID NOs 1 and 4 (FIG. 5A), and phosphorothioate analogs of the control oligonucleotide SEQ. ID. NO. 8 and MBOs SEQ ID NOs 2, 3, 5, and 6 (FIG. 5B) at the indicated times. Lanes labeled RNA+enzyme are the control lanes in the absence of antisense oligonucleotide.
Figure 5B:
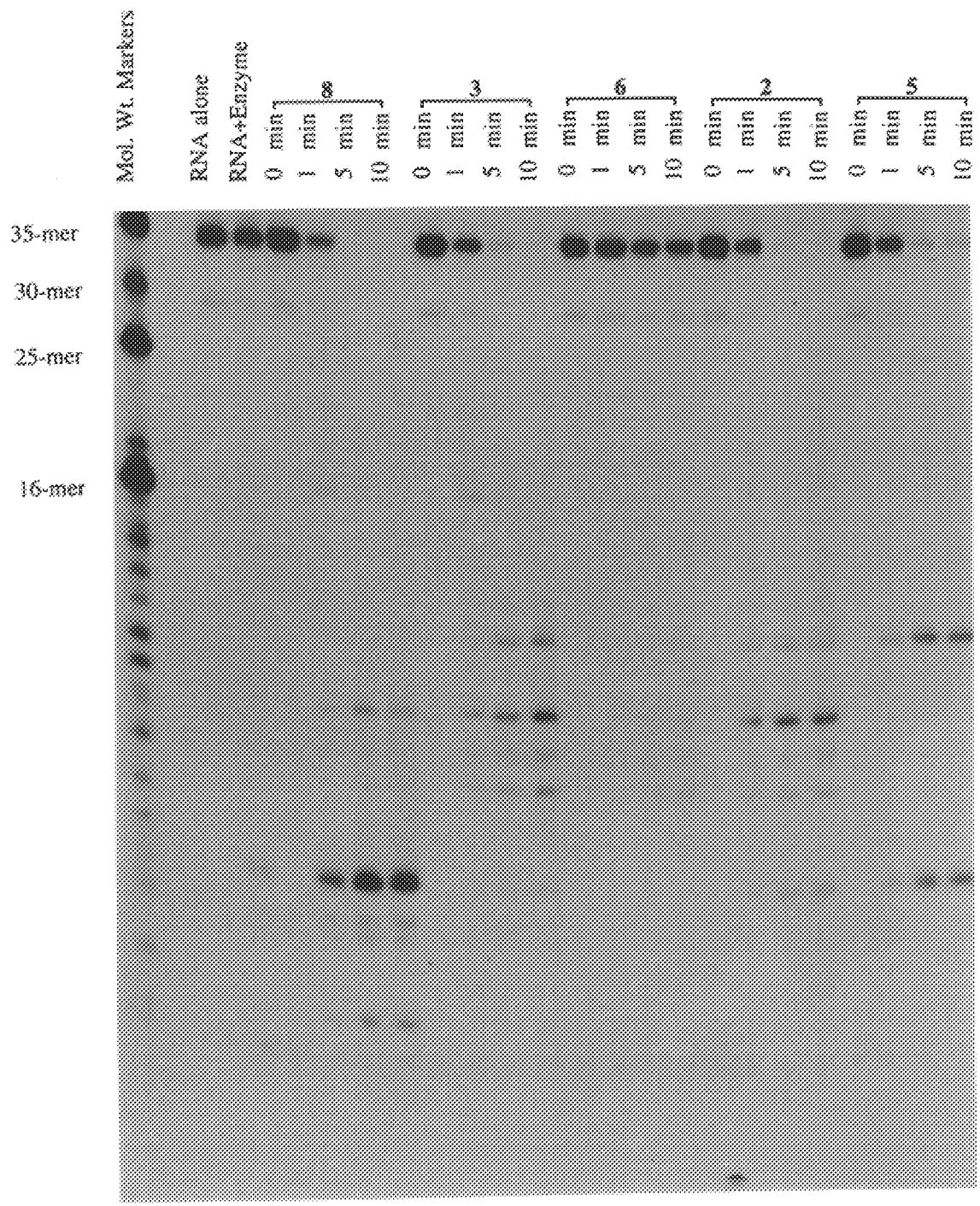

FIG. 5 shows RNase H hydrolysis pattern of the target RNA in the presence of control oligonucleotides and MBOs. Both phosphodiester and phosphorothioate analogs gave similar hydrolysis patterns. The rates of RNase H hydrolysis were different for phosphodiester and phosphorothioate analogs, however. (Agrawal et al., *Proc. Natl. Acad. Sci.* USA 87, 1401–1405 (1990). The RNA hydrolysis pattern was different in the presence of MBOs as compared to in the presence of control oligonucleotides. Absence of intense RNA hydrolysis bands in the lower half of the gel in the presence of MBOs SEQ ID NOs 1–3 (FIGS. 5 and 6) suggests that RNase H does not recognize the duplex region of 2'–5'-RNA with the RNA target strand. This result was verified by synthesizing an all 2'–5'-oligoribonucleotide and studying it for RNase H activation properties. The RNA hydrolysis pattern in the presence of SEQ ID NOs 1–3 also suggests that as a result of the presence of 2'–5' linkages at both the ends of the oligonucleotides, RNase H hydrolysis was confined to the middle of the RNA target strand, which portion hybridizes with 3'–5'-oligodeoxyribonucleotide segment of the MBOs. Hybridization of MBOs SEQ ID NOs 4–6 to the RNA target resulted in a slightly different RNase H hydrolysis pattern than in the case of MBOs SEQ ID NOs 1–3. RNase H hydrolysis was confined to the hetero-duplex region in the case of MBOs SEQ ID NO 4–6, also. Note that the lighter bands seen in the middle of the gel located around 16-mer marker in the lanes with control oligonucleotide and MBOs SEQ ID NOs 1–3 were absent in the lanes containing MBOs SEQ ID NOs 4–6. This is the location where the central 2'–5' RNA linkages are present in the oligonucleotides.

Example 7

Inhibition of HIV-1 Replication in Cell Culture

Oligonucleotides according to the invention were studied for their ability to inhibit HIV-1. HIV-1 inhibition assay was carried out as described previously. Kandimalla et al., *Nucleic Acids Res.*, supra). Briefly, serial dilutions of antisense oligonucleotides were prepared in 50 μl volumes of complete medium (RAMI-1640, 10% fetal bovine serum, 2 mM L-glutamine, 100 U/ml penicillin, 100 mg/ml streptomycin) in triplicate in 96-well plates. Virus diluted to contain a 90% CP dose of virus in 50 μl was added, followed by 100 μl 4×10$^5$/ml MT-4 cells in complete medium. The plates were incubated at 37° C. in 5% $CO_2$ for 6 days. MTT dye was added and quantified at $A_{540}$ and $A_{690}$ as described. The percent inhibition was calculated by the formula (experimental—virus control)/(medium control—virus control)×100.

We studied the inhibition of HIV-1 replication by MBOs in comparison to the phosphorothioate control oligonucleotide SEQ ID NO 8. All the oligonucleotides tested showed dose dependent inhibition of viral replication but with different $IC_{50}$ values. The results are shown in Table 1 as the concentration required to inhibit 50% ($IC_{50}$) viral replication. The control phosphorothioate oligonucleotide SEQ ID NO 8 has an $IC_{50}$ of 24.9 nM. A four fold higher concentration of MBO SEQ ID NO 2 was required to achieve $IC_{50}$. The phosphorothioate MBO SEQ ID NO 3 had an $IC_{50}$ of 29.8 nM comparable to that of the phosphorothioate control oligonucleotide SEQ ID NO 8. Although the phosphodiester analogs of MBOs showed longer stability against exo- and endonucleases and higher affinity to target RNA in vitro, they did not show significant activity against HIV-1. The lack of HIV-1 inhibition of phosphodiester MBOs could be mainly because of their susceptibility to endonucleases. MBO SEQ ID NO 5, which has nine 2'–5'- linkages, showed insignificant HIV-1 inhibition ($IC_{50}$ >800 nM).

Example 8

In Vitro Cell Proliferation Assay

Oligonucleotides have been shown to induce splenic cell proliferation and antibody production in vitro and in vivo (Zhao et al., Biochem. Pharmacol 51, 173–182 (1996); Krieg et al., Nature 374, 546–549 (1995)). These effects are sequence and chemical modification dependent (Zhao et al., supra), however. Recent studies suggest that unmethylated CpG dinucleotide motifs could be responsible for these effects (Krieg et al., supra). We studied whether the MBOs according to the invention would induce cell proliferation in vitro and compared the results with those of the control oligonucleotides SEQ ID NOs 7 and 8.

Cell proliferation assays were carried out as described earlier (Zhao et al., Biochem. Pharmacol 51, 173–182 (1996)). Spleen cells (4–5 week old male CD1 mouse, 20–22 gm, Charles River, Wilmington, Mass.) suspensions were prepared and plated in 96-well dishes at a density of 10$^6$ cells/ml in a final volume of 100 μl. The cells were incubated at 37° C. after adding 10 μl of oligonucleotides. After 44 hrs incubation, 1 μCi [3H]thymidine (Amersham, Arlington Heights, Ill.) was added and the cells were pulse-labeled for another 4 hrs. The cells were harvested by an automatic cell harvester and the filters were counted by a scintillation counter. All experiments were carried out in triplicate.

The results are shown in Table 1 as proliferatory index at 10 μg/ml concentration of the oligonucleotides. These results show that the phosphorothioate modification has greater cell proliferation effect than the PO backbone. Comparison of the data for oligonucleotides SEQ ID NO 3 (4.9), SEQ ID NO 6 (0.23) and SEQ ID NO 8 (6.16) further suggest that 2'–5'-RNA motifs reduced cell proliferation effect compared to the control phosphorothioate oligonucleotide. Sarin et al., supra.

Example 9

Clotting and Hemolytic Complement Assays

Phosphorothioate oligonucleotides are reported to show dose dependent prolongation of coagulation and activation of complement in vitro (Agrawal et al., Toxicology Letts. 82/83, 431–434 (1995)) and in vivo (Galbraith et al., Antisense Res. Dev., 4, 201–206 (1994)). These effects are reported to be sequence independent, but length dependent. Id. Recent studies suggest these effects could be modulated by backbone modifications. Agrawal et al., Toxicology Letts., supra. We studied the effects of MBOs on both coagulation and complement activities.

The activated partial thromboplastin time (aPTT) was performed with citrated normal human donor plasma in duplicate on an Electra 1000C (Medical Laboratory Automation, Mount Vernon, N.Y.) according to recommended procedures using Actin FSL (Baxter Dade, Miami, Fla.) and 2.5 mM calcium to initiate clot formation, which was measured photometrically. Normal plasma aPTT values ranged from 27 to 39 sec. Data were calculated as 50% of prolongation as compared to the saline control.

A $CH_{50}$ assay for complement lysis of sheep red blood cells (Colorado Serum Co., Denver, Col.) sensitized with anti-sheep red cell antibody (hemolysin; Diamedix, Miami, Fla.) as previously described (Mayer, In Experimental Immunochemistry, Kabat and Mayer eds., C. C. Thomas, Springfield, pp. 125–131 (1961)), was modified to test 1–200 dilutions of normal human serum interpreted. Hemoglobin release into cell-free supernates was measured spectrophotometrically at 541 nm. Data were calculated as 50% inhibition of lysis compared to saline control.

The results are presented in Table 1 (supra) as the oligonucleotide dose prolonging the aPTT (activated partial thromboplastin clotting time) 50% and inhibit complement lysis by 50%.

In coagulation assays, PO-oligonucleotides SEQ ID NOs 1, 4, and 7 showed negligible effect up to 100 μg/ml dose compared to a saline control experiment. The control Phosphorothioate-oligonucleotide SEQ ID NO 8 showed 50% larger prolongation at about 23 μg/ml dose. In the case of phosphorothioate-MBOs, a 2–3.5 fold higher concentration dose was required to attain the same extent of clotting prolongation compared to that of oligonucleotide SEQ ID NO 8. These results suggest that 2'–5'-RNA phosphorothioate modification has lower effect than 3'–5'-DNA phosphorothioates.

The PO-oligonucleotides of both control and MBOs showed minimal effects on complement hemolytic activity, whereas the control phosphorothioate-oligonucleotide SEQ ID NO 8 inhibited serum complement hemolytic activity. Phosphorothioate MBOs showed inhibition but at higher concentration than the control oligonucleotide SEQ ID NO 8. These results suggest that 2'–5'RNA phosphorothioates have lower complement activation property than the normal DNA phosphorothioates.

We claim:

1. An oligonucleotide in which at least two nucleotides are adjacent ribonucleotides, wherein adjacent ribonucleotides are linked together by a 2'–5' linkage and the remaining nucleotides are deoxyribonucleotides linked together by 3'–5' non-phosphodiester linkages.

2. The oligonucleotide according to claim 1, wherein at least one of the 2'–5' linkages is a non-phosphodiester internucleotide linkage.

3. The oligonucleotide according to claim 2, wherein the 2'–5' non-phosphodiester ribonucleotide linkage is a phosphorothioate internucleotide linkage.

4. The oligonucleotide according to claim 3, wherein all of the internucleotide linkages are phosphorothioate linkages.

5. The oligonucleotide according to claim 2, wherein the oligonucleotide is from about 12 to about 50 nucleotides long.

6. The oligonucleotide according to claim 3, wherein the oligonucleotide is from about 12 to about 50 nucleotides long.

7. The oligonucleotide according to claim 1, wherein at least two 2'–5'-linked ribonucleotides are located at the 3' end or both the 3' and 5' end of the oligonucleotide.

8. The oligonucleotide according to claim 7, wherein the oligonucleotide is from about 12 to about 50 nucleotides long.

9. The oligonucleotide according to claim 1, wherein at least two 2'–5' linked ribonucleotides are located in the middle of the oligonucleotide.

10. The oligonucleotide according to claim 9, wherein the oligonucleotide is from about 12 to about 50 nucleotides long.

11. The oligonucleotide according to claim 1, wherein the non-phosphodiester linkages are phosphorothioate linkages.

12. The oligonucleotide according to claim 11, wherein at least two 2'–5'-linked ribonucleotides are located at the 3' end or both the 3' and 5' end of the oligonucleotide.

13. The oligonucleotide according to claim 12, wherein the oligonucleotide is from about 12 to about 50 nucleotides long.

14. The oligonucleotide according to claim 11, wherein at least two 2'–5'-linked ribonucleotides are located in the middle of the oligonucleotide.

15. The oligonucleotide according to claim 14, wherein the oligonucleotide is from about 12 to about 50 nucleotides long.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:1:

CUCTCGCACC CATCTCTCTC CUUCT    25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:2:

CUCTCGCACC CATCTCTCTC CUUCT    25

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:3:

CUCTCGCACC CATCTCTCTC CUUCT    25

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:4:

CUCTCGCACC CAUCTCTCTC CUUCT                                                                     25

( 2 ) INFORMATION FOR SEQ ID NO:5:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:5:

CUCTCGCACC CAUCTCTCTC CUUCT                                                                     25

( 2 ) INFORMATION FOR SEQ ID NO:6:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:6:

CUCTCGCACC CAUCTCTCTC CUUCT                                                                     25

( 2 ) INFORMATION FOR SEQ ID NO:7:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:7:

CTCTCGCACC CATCTCTCTC CTTCT                                                                     25

( 2 ) INFORMATION FOR SEQ ID NO:8:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:8:

CTCTCGCACC CATCTCTCTC CTTCT                                                                     25

-continued ( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:9:

GGAGGCUAGA AGGAGAGAGA UGGGUGCGAG AGCGU      35

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:10:

CTAGAAGGAG AGAGATGGGT GCGAGAG      27

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:11:

AGAAGGAGAG AGAUGGGUGC GAGAG      25